(12) United States Patent
Dorantes et al.

(10) Patent No.: US 12,312,388 B2
(45) Date of Patent: May 27, 2025

(54) METHOD FOR INCREASING THE SECRETION LEVELS OF INTERLEUKIN 2 AND MUTEINS THEREOF BY INTRODUCING A POINT MUTATION

(71) Applicant: CENTRO DE INMUNOLOGIA MOLECULAR, Havana (CU)

(72) Inventors: Gertrudis Rojas Dorantes, Havana (CU); Kalet León Monzón, Havana (CU); Tania Carmenate Portilla, Havana (CU)

(73) Assignee: Centro de Inmunología Molecular, Havana (CU)

( * ) Notice: Subject to any disclaimer, the term of this patent is extended or adjusted under 35 U.S.C. 154(b) by 1313 days.

(21) Appl. No.: 16/461,258

(22) PCT Filed: Nov. 10, 2017

(86) PCT No.: PCT/CU2017/050007
§ 371 (c)(1),
(2) Date: May 15, 2019

(87) PCT Pub. No.: WO2018/091003
PCT Pub. Date: May 24, 2018

(65) Prior Publication Data
US 2019/0315826 A1 Oct. 17, 2019

(30) Foreign Application Priority Data
Nov. 15, 2016 (CU) .............. CU2016-0171

(51) Int. Cl.
*C07K 14/55* (2006.01)
*C12N 5/00* (2006.01)
*C12N 5/0781* (2010.01)
*C12N 5/0783* (2010.01)
*C12N 15/01* (2006.01)
*A61K 38/20* (2006.01)
*A61P 37/00* (2006.01)

(52) U.S. Cl.
CPC .......... *C07K 14/55* (2013.01); *C12N 5/0635* (2013.01); *C12N 5/0636* (2013.01); *C12N 15/01* (2013.01); *A61K 38/2013* (2013.01); *A61P 37/00* (2018.01); *C07K 2319/30* (2013.01); *C07K 2319/735* (2013.01)

(58) Field of Classification Search
CPC .... C07K 14/55; A61K 38/2013; C12N 15/01; C12N 2501/2302
See application file for complete search history.

(56) References Cited

U.S. PATENT DOCUMENTS

| | | | |
|---|---|---|---|
| 4,738,927 A * | 4/1988 | Taniguchi | C07K 14/55 435/317.1 |
| 8,759,486 B2 | 6/2014 | Monzón | |
| 9,206,243 B2 | 12/2015 | Monzón | |
| 2007/0014765 A1* | 1/2007 | Elias | A61K 47/60 424/85.2 |
| 2012/0244112 A1* | 9/2012 | Ast | C12N 15/09 536/23.4 |

FOREIGN PATENT DOCUMENTS

| | | |
|---|---|---|
| WO | WO 2005/007121 A2 | 1/2005 |
| WO | WO 2011/063770 A2 | 6/2011 |
| WO | WO 2005/086798 A2 | 9/2015 |

OTHER PUBLICATIONS

Tokuriki et al, 2009, Current Opinion in Structural Biology. 19: 596-604.*
Bhattacharya et al, 2017. Plos One. 12(3): e0171355, pp. 1-22 as printed.*
Buchli, Pamela J., et al., "The Functional Display of Interleukin-2 on Filamentous Phage", Archives of Biochemistry and Biophysics, vol. 339, No. 1, pp. 79-84, (Mar. 1, 1997).
Carmenate, Tania, et al., "Human IL-2 Mutein with Higher Antitumor Efficacy Than Wild Type IL-2", The Journal of Immunology, vol. 190, pp. 6230-6238 (2013).
Cha Hyung Joon, et al., "Comparative Production of Human Interleukin-2 fused with Green Fluorescent Protein in Several Recombinant Expression Systems", Biochemical Engineering Journal 24, pp. 225-233 (2005).
Devos, R., et al., "Molecular Cloning of Human Interleukin 2 cDNA and Its Epression in *E. coli*", Nucleic Acids Research vol. 11, No. 13 (1983).
Drew, Yvette, "The Development of PARP Inhibitors in Ovarian Cancer: From Bench to Bedside", British Journal of Cancer 113, S3-S9 (2015).
Halfmann, Gabriele, et al., "Targeting of Interleukin-2 to the Periplasm of *Escherichia coli*", Journal of General Microbiology vol. 139, pp. 2465-2473 (1993).

(Continued)

*Primary Examiner* — Zachary C Howard
(74) *Attorney, Agent, or Firm* — Foley Hoag LLP; Philip S. Choi; Erin M. Foley

(57) ABSTRACT

The present invention relates to the field of Biotechnology, particularly to a method based on the introduction of a single mutation in the genes encoding the human IL-2 and the muteins derived thereof that results in increased secretion levels in different hosts without affecting their biological functions. In particular, these mutations are based on a non-conservative change in the amino acid located in position 35 in the primary sequence of human IL-2, preferably the substitutions are K35E, K35D and K35Q. Another object of the present invention are the expression systems used to obtain both the recombinant human IL-2 and the muteins derived thereof using the method described in this invention. The above-mentioned method is useful to improve the production efficiency of the recombinant human IL-2 and the muteins derived thereof both at laboratory and industrial scales. The proteins obtained using this method can be used for therapeutic purposes as well as in the in vitro expansion of T cells for adoptive transfer therapies.

18 Claims, 7 Drawing Sheets

Specification includes a Sequence Listing.

(56) References Cited

OTHER PUBLICATIONS

Hartemann, Agnes, et al., "Low-dose interleukin 2 in Patients with Type 1 Diabetes: A phase 1/2 Randomised, Double-Blind, Placebo-Controlled Trial", Lancet diabetes Endocrinology vol. 1, pp. 295-305 (Dec. 2013).

Hoyer, Katrina K., et al., "Interleukin-2 in the Development and Control of Inflammatory Disease", Immunological Reviews, 226: pp. 19-28 (2008).

Klapper, Jacob A., et al., "High-dose Interleukin-2 for the Treatment of Metastatic Renal Cell Carcinoma", Cancer vol. 113, No. 2, pp. 293-301 (Jul. 15, 2008).

Koreth, John, et al., "Interleukin-2 and Regulatory T Cells in Graft-versus-Host Disease", The New England Journal of Medicine, vol. 365, No. 22, pp. 2055-2066 (Dec. 1, 2011).

Levin, Aron M., et al., "Exploitig a natural Conformational Switch to Engineer and Interleukin-2 'Superkine'", Nature vol. 484, pp. 529-533 (Apr. 26, 2012).

Malek, Thomas R., et al., "Tolerance, Not Immunity, Crucially Depends on IL-2", Nature Review Immunology, vol. 4, pp. 665-674 (Sep. 2004).

Malek, Thomas R., "The Biology of Interleukin-2", Annual Review of Immunology, vol. 26, pp. 453-479 (2008).

Malek, Thomas R., et al., "Interleukin-2 Receptor Signaling: At the Interface between Tolerance and Immunity", Immunity Review, 33: 153-165, (Aug. 27, 2010).

Robbens, J., et al., "Improved Periplasmic Production of Biologically Active Murine Interleukin-2 in *Escherichia coli* Through a Single Amino Acid Change at the Cleavage Site", Process Biochemistry 41:1343-1356 (2006).

Saadoun, David, et al., "Regulatory T-Cell Responses to Low-Dose Interleukin-2 in HCV-Induced Vasculitis", The New England Journal of Medicine, 365: 2067-2077 (Dec. 1, 2011).

Sauve, K., et al., "Localization in Human Interleukin 2 of the Binding Site to the a Chain (p55) of the Interleukin 2 Receptor", Proc. Nati. Acad. Sci USA, vol. 88, pp. 4636-4640 (Jun. 1991).

Shanafelt, Armen, B., et al., "A T-cell-selective Interleukin 2 Mutein Exhibits Potent antitumor Activity and is Well Tolerated in Vivo", Nature Biotechnology vol. 18, pp. 1197-1202 (Nov. 2000).

Smith, Kendall, A., " T-Cell Growth Factor", Immunological Review, vol. 51, pp. 337-357 (1980).

Vispo, N.S., et al., "Displaying Human Interleukin-2 on the Surface of Bacteriophage", Immunotechnology 3: 185-193 (1997).

Weigel, Ulrich, et al., "Mutant Proteins of Human Interleukin 2 Renaturation Yield, Proliferative Activity and Receptor Binding", Eur. J. Biochem., 180: 295-300 (1989).

Weir, Malcolm P., et al., "Purification and Renaturation of Recombinant Human Inteleukin-2", Biochemistry Journal vol. 245, pp. 85-91 (1987).

Extended European Search Report for EP Application No. 17817648.3 dated Apr. 28, 2020.

International Search Report and Written Opinion for International Application No. PCT/CU2017/050007 dated May 24, 2018.

* cited by examiner

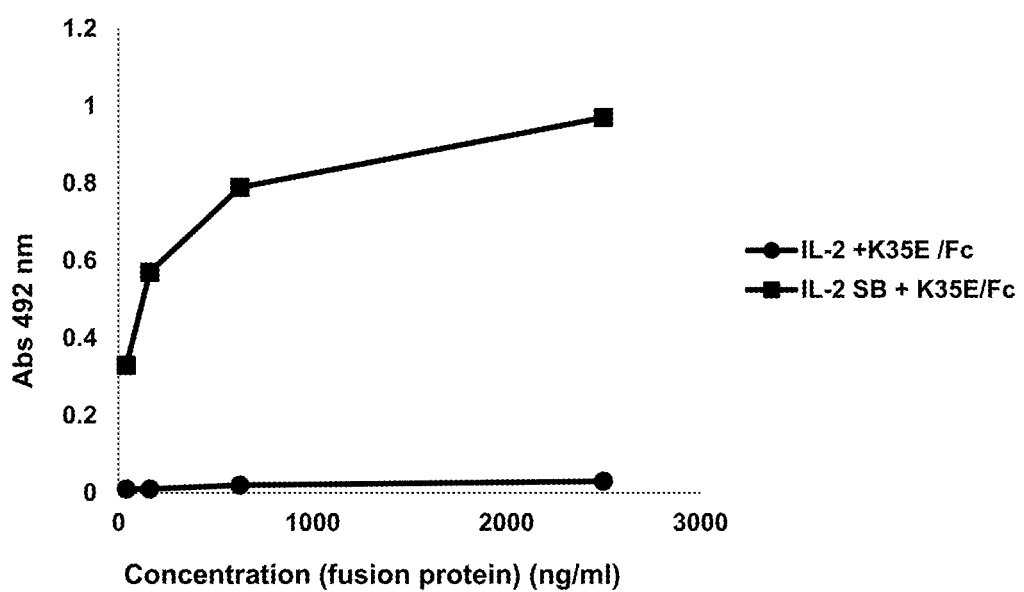
Figura 7

SEQUENCE LISTING

<160> NUMBER OF SEQ ID NOS: 18

<210> SEQ ID NO 1
<211> LENGTH: 133
<212> TYPE: PRT
<213> ORGANISM: Artificial Sequence
<220> FEATURE:
<223> OTHER INFORMATION: by DNA recombinant technology

<400> SEQUENCE: 1

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Glu Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130
```

<210> SEQ ID NO 2
<211> LENGTH: 133
<212> TYPE: PRT
<213> ORGANISM: Artificial Sequence
<220> FEATURE:
<223> OTHER INFORMATION: by DNA recombinant technology

<400> SEQUENCE: 2

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Asp Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130
```

<210> SEQ ID NO 3
<211> LENGTH: 133

```
<212> TYPE: PRT
<213> ORGANISM: Artificial Sequence
<220> FEATURE:
<223> OTHER INFORMATION: by DNA recombinant technology

<400> SEQUENCE: 3

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Gln Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 4
<211> LENGTH: 133
<212> TYPE: PRT
<213> ORGANISM: Artificial Sequence
<220> FEATURE:
<223> OTHER INFORMATION: by DNA recombinant technology

<400> SEQUENCE: 4

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Glu Leu Thr Ala Met Leu Thr Ala Lys Phe Ala Met Pro Lys
            35                  40                  45

Lys Ala Thr Glu Leu Lys His Leu Gln Cys Leu Glu Glu Ala Leu Lys
 50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 5
<211> LENGTH: 133
<212> TYPE: PRT
<213> ORGANISM: Artificial Sequence
<220> FEATURE:
<223> OTHER INFORMATION: by DNS recombinant technology
```

<400> SEQUENCE: 5

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Asp Leu Thr Ala Met Leu Thr Ala Lys Phe Ala Met Pro Lys
        35                  40                  45

Lys Ala Thr Glu Leu Lys His Leu Gln Cys Leu Glu Glu Ala Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 6
<211> LENGTH: 133
<212> TYPE: PRT
<213> ORGANISM: Artificial Sequence
<220> FEATURE:
<223> OTHER INFORMATION: by DNA recombinant technology

<400> SEQUENCE: 6

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Gln Leu Thr Ala Met Leu Thr Ala Lys Phe Ala Met Pro Lys
        35                  40                  45

Lys Ala Thr Glu Leu Lys His Leu Gln Cys Leu Glu Glu Ala Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 7
<211> LENGTH: 133
<212> TYPE: PRT
<213> ORGANISM: Artificial Sequence
<220> FEATURE:
<223> OTHER INFORMATION: by DNA recombinant technology

<400> SEQUENCE: 7

Ala Pro Thr Ser Ser Ser Thr Lys Lys Thr Gln Leu Gln Leu Glu His
1               5                   10                  15

```
Leu Leu Leu Asp Leu Val Met Ile Leu Asn Gly Ile Asn Asn Tyr Lys
            20                  25                  30

Asn Pro Glu Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Ala Ser Ile
            115                 120                 125

Asp Gly Thr Leu Thr
            130

<210> SEQ ID NO 8
<211> LENGTH: 133
<212> TYPE: PRT
<213> ORGANISM: Artificial Sequence
<220> FEATURE:
<223> OTHER INFORMATION: by DNA recombinant technology

<400> SEQUENCE: 8

Ala Pro Thr Ser Ser Ser Thr Lys Lys Thr Gln Leu Gln Leu Glu His
1               5                   10                  15

Leu Leu Leu Asp Leu Val Met Ile Leu Asn Gly Ile Asn Asn Tyr Lys
            20                  25                  30

Asn Pro Asp Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Ala Ser Ile
            115                 120                 125

Asp Gly Thr Leu Thr
            130

<210> SEQ ID NO 9
<211> LENGTH: 133
<212> TYPE: PRT
<213> ORGANISM: Artificial Sequence
<220> FEATURE:
<223> OTHER INFORMATION: by DNA recombinant technology

<400> SEQUENCE: 9

Ala Pro Thr Ser Ser Ser Thr Lys Lys Thr Gln Leu Gln Leu Glu His
1               5                   10                  15

Leu Leu Leu Asp Leu Val Met Ile Leu Asn Gly Ile Asn Asn Tyr Lys
            20                  25                  30

Asn Pro Gln Leu Thr Arg Met Leu Thr Phe Lys Phe Tyr Met Pro Lys
        35                  40                  45
```

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Ala Ser Ile
            115                 120                 125

Asp Gly Thr Leu Thr
        130

<210> SEQ ID NO 10
<211> LENGTH: 133
<212> TYPE: PRT
<213> ORGANISM: Artificial Sequence
<220> FEATURE:
<223> OTHER INFORMATION: by DNA recombinant technology

<400> SEQUENCE: 10

Ala Pro Thr Ser Ser Ser Thr Lys Lys Thr Gln Leu Gln Leu Glu His
 1               5                  10                  15

Leu Asn Leu Asp Leu Gln Met Ile Leu Asn Gly Ile Asn Asn Tyr Lys
                 20                  25                  30

Asn Pro Glu Leu Thr Arg Met Leu Thr Phe Lys Phe Tyr Met Pro Lys
                 35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Tyr Ser Ile
            115                 120                 125

Ile Arg Thr Leu Thr
        130

<210> SEQ ID NO 11
<211> LENGTH: 133
<212> TYPE: PRT
<213> ORGANISM: Artificial Sequence
<220> FEATURE:
<223> OTHER INFORMATION: by DNA recombinant technology

<400> SEQUENCE: 11

Ala Pro Thr Ser Ser Ser Thr Lys Lys Thr Gln Leu Gln Leu Glu His
 1               5                  10                  15

Leu Asn Leu Asp Leu Gln Met Ile Leu Asn Gly Ile Asn Asn Tyr Lys
                 20                  25                  30

Asn Pro Asp Leu Thr Arg Met Leu Thr Phe Lys Phe Tyr Met Pro Lys
                 35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu

```
            65                  70                  75                  80
Arg Pro Arg Asp Leu Ile Ser Asn Ile Asn Val Ile Val Leu Glu Leu
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Tyr Ser Ile
                115                 120                 125

Ile Arg Thr Leu Thr
            130

<210> SEQ ID NO 12
<211> LENGTH: 133
<212> TYPE: PRT
<213> ORGANISM: Artificial Sequence
<220> FEATURE:
<223> OTHER INFORMATION: by DNA recombinant technology

<400> SEQUENCE: 12

Ala Pro Thr Ser Ser Ser Thr Lys Lys Thr Gln Leu Gln Leu Glu His
1               5                   10                  15

Leu Asn Leu Asp Leu Gln Met Ile Leu Asn Gly Ile Asn Asn Tyr Lys
                20                  25                  30

Asn Pro Gln Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Tyr Ser Ile
                115                 120                 125

Ile Arg Thr Leu Thr
            130

<210> SEQ ID NO 13
<211> LENGTH: 133
<212> TYPE: PRT
<213> ORGANISM: Artificial Sequence
<220> FEATURE:
<223> OTHER INFORMATION: by DNA recombinant technology

<400> SEQUENCE: 13

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Glu Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                    85                  90                  95
```

```
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
        115                 120                 125
Ile Ser Thr Leu Thr
        130

<210> SEQ ID NO 14
<211> LENGTH: 133
<212> TYPE: PRT
<213> ORGANISM: Artificial Sequence
<220> FEATURE:
<223> OTHER INFORMATION: by DNA recombinant technology

<400> SEQUENCE: 14

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Asp Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Phe
65                  70                  75                  80
Asp Pro Arg Asp Val Val Ser Asn Ile Asn Val Phe Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
        115                 120                 125
Ile Ser Thr Leu Thr
        130

<210> SEQ ID NO 15
<211> LENGTH: 133
<212> TYPE: PRT
<213> ORGANISM: Artificial Sequence
<220> FEATURE:
<223> OTHER INFORMATION: by DNA recombinant technology

<400> SEQUENCE: 15

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Gln Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Phe
65                  70                  75                  80
Asp Pro Arg Asp Val Val Ser Asn Ile Asn Val Phe Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
        115                 120                 125
```

Ile Ser Thr Leu Thr
    130

<210> SEQ ID NO 16
<211> LENGTH: 133
<212> TYPE: PRT
<213> ORGANISM: Artificial Sequence
<220> FEATURE:
<223> OTHER INFORMATION: by DNA recombinant technology

<400> SEQUENCE: 16

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Glu Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Ala Leu Asn Leu Ala Pro Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 17
<211> LENGTH: 133
<212> TYPE: PRT
<213> ORGANISM: Artificial Sequence
<220> FEATURE:
<223> OTHER INFORMATION: by DNA recombinant technology

<400> SEQUENCE: 17

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Asp Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Ala Leu Asn Leu Ala Pro Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

```
<210> SEQ ID NO 18
<211> LENGTH: 133
<212> TYPE: PRT
<213> ORGANISM: Artificial Sequence
<220> FEATURE:
<223> OTHER INFORMATION: by DNA recombinant technology

<400> SEQUENCE: 18

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Gln Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Ala Leu Asn Leu Ala Pro Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
            130
```

METHOD FOR INCREASING THE SECRETION LEVELS OF INTERLEUKIN 2 AND MUTEINS THEREOF BY INTRODUCING A POINT MUTATION

CROSS-REFERENCE TO RELATED APPLICATIONS

This application is a National Stage Application that claims a benefit of priority from Application No. PCT/CU2017/050007 filed Nov. 10, 2017, which claims priority to Application No. CU 2016-0171, filed Nov. 15, 2016, the disclosures of which are herein incorporated in their entirety.

SEQUENCE LISTING

The instant application contains a Sequence Listing, which has been submitted electronically in ASCII format and is hereby incorporated by reference in its entirety. Said ASCII copy, created on May 24, 2018, is named IAC-00501_SL.txt and is 23,070 bytes in size.

SCOPE OF THE TECHNIQUE

The present invention relates to the field of Biotechnology. Particularly to a method for the introduction of mutations in the gene of interleukin-2 (IL-2) that leads to an increase in the secretion levels of said molecule and the family of immunomodulatory muteins derived thereof without affecting their biological functions.

BACKGROUND

IL-2, originally described as a growth factor for T cells (Smith, K. A. Immunol. Rev. 51: 337-357, 1980), has subsequently emerged as a regulator with dual functions within the immune response (Malek, T. R. Annu. Rev. Immunol. 26: 453-479, 2008; Hoyer K. K. et al, Immunol. Rev. 226: 19-28, 2008), which exhibits the ability to promote or negatively modulate the effector functions of the immune system. Its main role is currently considered related to the maintenance of immunological tolerance (Malek, T. R. & Bayer, A. L. Nat. Rev. Immunol. 4: 665-674, 2004) through the stimulation of regulatory T cells, which constitutively express high levels of the alpha chain of the IL-2 receptor. Although the beta and gamma subunits form the intermediate affinity dimeric receptor constitutively present in the effector cells of the immune system, the constitutive presence of high levels of the alpha chain gives the regulatory T cells a high affinity trimeric receptor that allows the preferential use of the cytokine by this cell population. (Malek, T. R. & Castro, I. Immunity. 33: 153-165, 2010).

The functional dichotomy of IL-2 has been exploited to produce opposite therapeutic effects on the immune system and modulate the immune response in the desired sense in different scenarios. Its immunopotentiating capacity has been used to stimulate anti-tumor responses (Klapper, J. A. et al, Cancer. 113: 293-301, 2008). On the other hand, the ability of IL-2 to stimulate preferentially T regulatory cells has been exploited through the application of low doses, insufficient to stimulate effector T cells or produce toxic effects, for the control of autoimmune disorders (Hartemann, A. et al, Lancet Diabetes Endocrinol. 1: 295-305, 2013) and inflammatory (Saadoun, D. et al, N. Engl. J. Med. 365: 2067-2077, 2011), and of graft versus host disease (Koreth, A. et al, N. Engl. J. Med. 365: 2055-2066, 2011).

The segregation of the interactions of IL-2 through the introduction of mutations in the different binding interfaces with the subunits of the receptor has been proposed as a way to obtain muteins with different immunomodulatory properties. The selective perturbation of the interface with the alpha chain by directed mutagenesis has allowed to obtain a molecule called no-alpha with reduced capacity to stimulate the regulatory T cells, but which retains its agonist action on the effector cells that carry the beta/gamma dimeric receptor (Carmenate, T. et al, J. Immunol. 190: 6230-6238, 2013; U.S. Pat. No. 9,206,243 B2). This molecule has a strong antitumor effect in mice. On the other hand, the disruption by mutagenesis of the IL-2 interface with the beta and/or gamma subunits can generate IL-2 receptor antagonists that selectively modulate the stimulation of different cell populations (Shanafelt, A. B. et al, Nat. Biotechnol. 18: 1197-1202, 2000; WO 2011/063770). Examples of this type of molecules are the muteins M1 and M2 described in U.S. Pat. No. 8,759,486 B2.

In addition to the muteins with loss of their interaction capacity, mutated variants of IL-2 with superagonist properties due to the increase of their binding capacity to one or another subunit of the receptor have also been described The increase in affinity for the beta subunit leads to the production of molecules that potently stimulate the effector cells and have a strong antitumor effect (Levin, A. M. et al, Nature. 484: 529-533, 2012). On the other hand, the increased affinity of IL-2 for the alpha subunit of the receptor has given rise to other superagonist variants with superior ability to stimulate the proliferative response of T cells in vitro (WO 2005/007121).

The IL-2-derived muteins described above have been obtained through rational design, in silico screening and the directed evolution of IL-2 displayed on the surface of yeast cells. Although the display of biologically active IL-2 on filamentous phages has been achieved (Buchli, P. J. et al, Arch. Biochem. Biophys. 339: 79-84, 1997; Vispo, N. S. et al, Immunotechnology 3: 185-193, 1997), this technological platform has not yet been exploited for the selection of new variants of the cytokine with modified properties.

Beyond the immunomodulatory properties of IL-2 and its derived muteins, an essential element for their therapeutic exploitation is the development of systems that allow it to be obtained in sufficient quantities. In particular, on a laboratory scale, on an industrial scale or by transfection or transduction of normal and/or tumor cells or tissues.

The predominant pathway for the recombinant production of IL-2 and other related molecules has been the expression in the cytoplasm of E. coli forming inclusion bodies, followed by in vitro re-naturalization procedures (Devos, R. et al, Nucl. Acids Res. 11: 4307-4323, 1983; Weir, M. P. & Sparks, J., Biochem. J. 245: 85-91, 1987). Despite the utility already demonstrated for this strategy, the exploration of other expression systems that lead from the beginning to obtaining correctly folded molecules very similar to natural IL-2, has continued. The secretion of IL-2 in some of these expression systems has been limited by the tendency of IL-2 to aggregate (Halfmann, G. et al, J. Gen. Microbiol. 139: 2465-2473, 1993; Cha, H. J. et al, Biochem. Eng. J. 24: 225-233, 2005).

Surprisingly, the inventors of the present invention found several mutations not previously described or predictable from the analysis of the crystal structure of human IL-2, whose introduction increases the ability of different cell types to secrete recombinant human IL-2 and multiple muteins derived from it that have specific immunomodulatory properties. This finding provides the basis for the use of these mutations at a productive scale.

SUMMARY OF THE INVENTION

In one embodiment, the present invention is related to method that leads to increased secretion levels of recombinant human IL-2 in different hosts without affecting their biological functions. Said method is based on the introduction of unique mutations in the genes encoding human IL-2 and other polypeptides derived from it, which include but are not limited to muteins derived from human IL-2 designed to act as antagonists, superagonistas or selective agonists. The increase in the secretion levels of said proteins when the method of the present invention is used is at least three times higher in relation to the unmutated counterparts. In the present invention derived muteins refers to those which have more than 90% identity with human IL-2.

The method of the present invention relates to mutations that lead to a non-conservative change of the amino acid occupying the position 35 of the primary protein sequence (Lys in the original sequence), preferably the K35E, K35D and K35Q substitutions.

Particularly, the present invention relates to the proteins obtained according to the method described here which are selected from the group comprising SEQ ID NO. 1 to 18.

Also the object of the present invention are genetic constructs that include the above-described mutated genes fused to other nucleotide sequences that encode the synthesis of fusion proteins formed by IL-2 or other immunomodulatory polypeptides derived therefrom and additional protein sequences. Additional protein sequences include but are not limited to the capsid proteins of filamentous phages, albumin, Fc region of the antibodies, whole antibodies or antibody fragments that include their variable domains.

In a particular embodiment, the hosts that are used to obtain the molecules described above include but are not limited to *E. coli*, yeast and mammalian cells such as HEK-293, CHO, NSO, among others. The method of the present invention is useful for improving the efficiency of the production of IL-2 and other polypeptides derived therefrom, both at the laboratory and industrial scale. The proteins obtained by the method of the present invention can be used for therapeutic purposes. In another embodiment, the objective of the present invention is to modify the physiology of normal and tumoral cells and/or tissues through the expression of human IL-2 and/or the family of immunomodulatory muteins derived therefrom (alone or fused to other proteins), both in vitro and in vivo. Example the transduction of T lymphocytes, B lymphocytes or NK cells for adoptive transfer therapies; or the direct transduction/transfection of a tumor tissue. The method of the present invention is useful for increasing the secretion of the molecules of interest in these contexts.

DETAILED DESCRIPTION OF THE INVENTION

The present invention relates to a method that leads to increased levels of secretion of recombinant human IL-2 in different hosts without affecting their biological functions. Said method is based on the introduction of unique mutations in the genes encoding human IL-2 and other polypeptides derived therefrom, which include but are not limited to muteins derived from human IL-2 designed to act as antagonists, superagonists or selective agonists.

Identification of Mutations Increasing the Capacity of Proteins Derived from Human IL-2 to be Displayed on Filamentous Phages.

The selection of polypeptides derived from human IL-2, with unique mutations that lead to the increase of their display levels on filamentous phages can be made from libraries of more than $10^8$ molecules presented on filamentous phages. Genes corresponding to said polypeptides can be inserted into phagemid type expression vectors (fused to one of the genes encoding filamentous phage capsid proteins) and used for the production of viral particles that display the protein variants on their surface. The starting libraries may include different degrees of diversification throughout the entire sequence or in a set of pre-defined positions. Each of the original residues in these positions can be replaced by a mixture of the 20 aminoacids or by a subset of selected residues. Diversification can be achieved through random or site-directed mutagenesis.

The selection of phages with increased levels of display of human IL-2 can be based on the incubation of phage mixtures from libraries in contact with a selector molecule immobilized on a solid surface, the elimination of unbound phages by washing, and the elution of bound phages under conditions that interfere with protein interactions. As a selector molecule, one of the recombinant IL-2 receptor subunits or a monoclonal antibody directed against IL-2 or against a peptide genetically fused thereto can be used. Several successive cycles of selection can be made under similar conditions. Analysis of the DNA sequences inserted in the selected phagemids can reveal regularities that lead to the identification of those more abundant substitutions and potentially related to the increase in display capacity on the phages.

The levels of display of the mutated variants of IL-2 can be evaluated through binding assays such as ELISA, on an immobilized capture molecule that recognizes indistinctively the different IL-2 mutated variants and the native reference. As a capture molecule for this type of assays, an antibody against a marker peptide sequence genetically fused to IL-2 variants, such as the c-myc peptide, which is fused to all foreign proteins in the expression system based on the phagemid vector pCSM, is preferred. The generality of the mutations' effects identified in the screening described above on the IL-2 derived muteins family can be demonstrated through the introduction of said changes in the sequence of the different mutated variants described for human IL-2, which include a variable number of substitutions of diverse nature throughout its sequence aimed at selectively affecting the interactions with the different subunits of the IL-2 receptor, with the subsequent modification of their immunomodulatory functions. All these modified muteins are displayed on filamentous phages, by inserting their coding genes in phagemid vectors. Evaluation of each mutein display levels on filamentous phages can be performed by ELISA as described for IL-2. As a reference for calculating the magnitude of phage display increase associated with the introduction of the changes identified as part of the present invention, the original muteins are used without any additional change and display on phages. Alternatively, the method of the present invention could be performed by exploiting other platforms of combinatorial biology, such as display on yeast or mammalian cells, in order to select variants of IL-2 and/or its derived muteins with increased levels of presentation on the cell membrane. From the selection process described above, recurrent non-conservative mutations can emerge at position 35 (particularly K35E, K35D and K35Q).

Use of Identified Mutations to Increase the Secretion Levels of Human IL-2 and Muteins Derived Thereof, as Soluble Proteins and their Re-Naturalization from Inclusions Bodies Once a group of mutations that result in an increased display on filamentous phages of the human IL-2 and its derived muteins is identified, the effect of these same changes on the secretion of soluble proteins can be demonstrated, by introducing them into the corresponding coding genes cloned in soluble expression vectors for yeast or mammalian cells. Evaluation of concentrations of the proteins secreted to the supernatant by the host cells containing said expression vectors allows to demonstrate the increase in the secretion of IL-2 and its derived muteins associated with the introduction of the mutations that the method of the present invention uses, in comparison with its original counterparts that do not include said changes.

Alternatively, the increased production of human IL-2 and its derived muteins should be verified from transfection and/or transduction of normal and/or tumor cells and/or tissue in vivo or in vitro.

The studies described above that use the method of the present invention can be performed with IL-2 and its derived muteins alone or fused to additional polypeptide sequences, such as albumin, Fc region of human immunoglobulins, whole antibodies or antibody fragments based on its variable regions.

The mutations described in the present invention can also be used to improve the processes of in vitro re-naturalization of human IL-2 and its derived muteins, obtained as inclusion bodies in the cytoplasm of E. coli. The increase in the efficiency of re-naturalization can be evaluated by measuring the specific biological activity per protein mass by comparison to the unmutated variant.

Demonstration of Compatibility of the Used Mutations with Biological Functions of the IL-2 and the Selective Modulation of its Interactions with the Receptor Subunits.

The evaluation of biological activity of IL-2 variants modified by the present invention method can cover in vitro and in vivo techniques directed to evidence the preservation of their ability to induce proliferation, differentiation and activation of different cell types, such as T lymphocyte subpopulations, NK cells and cell lines of lymphoid origin dependent on IL-2 for their growth. The effect of native IL-2 on the proliferation of T lymphocytes expressing the trimeric receptor can be determined by the in vitro assay of CTLL-2 cell line proliferation using the colorimetric technique of Alamar blue reduction or by flow cytometry. The in vitro effect of native IL-2 on the differentiation of T CD4+ lymphocytes to T regulatory lymphocytes and the capacity of this molecule to expand and activate NK cells in vitro, are determined by flow cytometry.

The compatibility of mutations used in the method of the present invention with the selective modulation of IL-2 interaction with its receptor can be evidenced by introducing said changes on the framework of muteins previously designed and/or selected to increase or decrease their binding capacity to any of the subunits of the IL-2 receptor. The occurrence of the desired changes in the binding properties can be demonstrated through the direct determination of them in ELISA experiments on microtitre plates coated with each of the receptor subunits. The previously described assays used to characterize the immunomodulatory and/or antitumor activity of the different muteins in vitro and in vivo can be used as additional verification tools. In the case of no-alpha mutein (Carmenate, T. y otros, J. Immunol. 190: 6230-6238, 2013), it can be verified that it maintains the same capacity as native IL-2 to stimulate in vitro the proliferation of T CD8+ lymphocytes. In the case of a mutein with increased binding capacity to the beta subunit of the receptor and that has superagonist activity (super-beta mutein), it can be verified that it maintains higher capacity than native IL-2 to stimulate in vitro NK cell proliferation. In both cases proliferation can be determined by flow cytometry. The differential effect on the proliferation of populations in vivo can be determined by experiments of bromodeoxyuridine incorporation. It can be demonstrated that both muteins induce greater antitumor effect in vivo than native IL-2, in the experimental metastasis model that uses the MB16F0 melanoma line.

BRIEF DESCRIPTION OF THE FIGURES

FIG. 7. Compatibility of the replacement K35E with the increase in binding ability to the IL-2 receptor beta subunit already described for an IL-2-derived mutein (ELISA).

EXAMPLES

Example 1. Selection and Characterization of Filamentous Phages Displaying Functional Mutated Human IL-2

A soft randomization library targeting several positions of human IL-2 was constructed. Selected positions included those having residues with side chains contributing to the alpha subunit receptor interface (K35, R38, T41, F42, K43, F44, Y45, E61, E62, K64, P65, E68, V69, N71, L72, Q74 and Y107). Human IL-2 was diversified by Kunkel mutagenesis with spiked mutagenic oligonucleotides keeping 85% of the original nucleotide at each targeted position, plus 15% of the equimolar mixture of the remaining three nucleotides, in order to introduce a moderate degree of diversity in all the selected region. The resulting $10^9$ clone's library thus contained as a whole the 20 amino acids at each position of the interface, while each molecule within the library only had a few replacements, restricting the search for new polypeptides to the functional sequence space closer to the starting molecule. Library phages were purified by precipitation with polyethylene glycol using established procedures (Marks, J. et al, J. Mol. Biol. 222: 581-597, 1991). Purified viral particles were incubated on immunotubes (Nunc, Denmark) coated with the recombinant alpha IL-2 receptor subunit (R&D), in order to isolate functional mutated IL-2 variants due to their ability to be displayed on phages. Two independent panning procedures were performed on human and mouse IL-2 receptor subunits. After washing non-bound phages, bound phages were eluted by adding a basic triethylamine solution. TG1 bacteria were infected with the selected phages, which were amplified using M13KO7 helper phage and used as starting material for a new selection round. Four phage selection rounds were performed. Sequencing of the inserts in the selected phagemids (from the third and fourth selection rounds) revealed similarities in the resulting mutated variants. Despite the predominance of the original non-mutated IL-2 gene (highly represented in the original library), there was a minor proportion of variants having the replacements K35E, K35D and K35Q, showing the influence of non-conservative changes at position 35 in the display of functional IL-2 on filamentous phages. K35E was the most frequent replacement. This finding was surprising, as the analysis of the crystal structure of the IL-2/receptor complex (PDB codes3B51 and 2ERJ) points to the involvement of the original K35 residue in ionic interactions in the polar peripheral region of the interface with the alpha subunit. The ability of the non-conservative replacements (charge inversion in two of the cases) to keep the interaction with the selector molecule was thus unexpected.

Example 2. Increase in the Secretion and Phage Display of Human IL-2 with Non-Conservative Changes at Position 35

Figure 1:
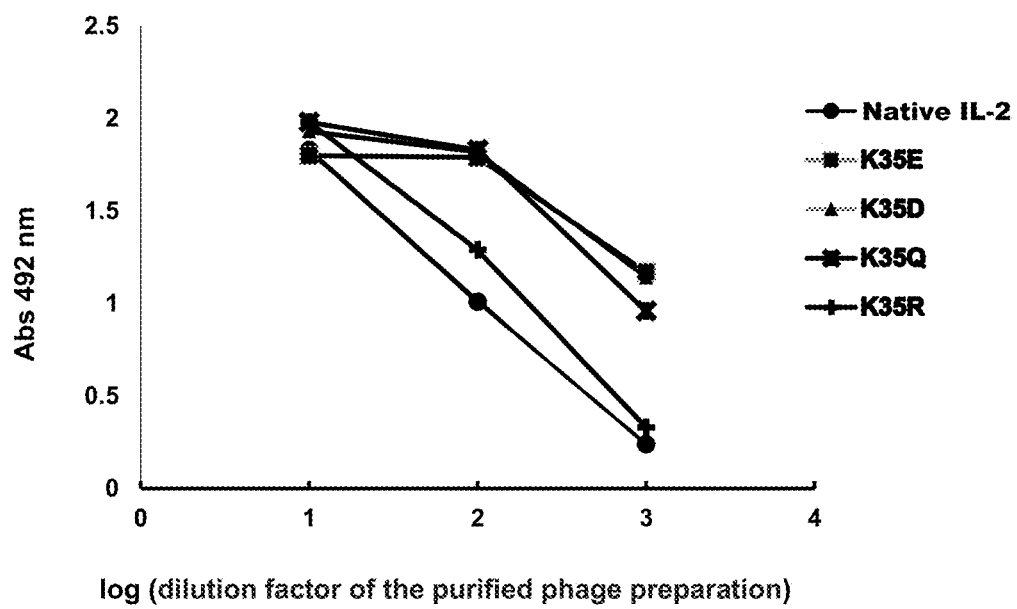
FIG. 1. ELISA evaluation of phage display levels of mutated IL-2. All the phage preparations were adjusted to an equivalent concentration of $10^{13}$ viral particles/ml.
Figure 2:
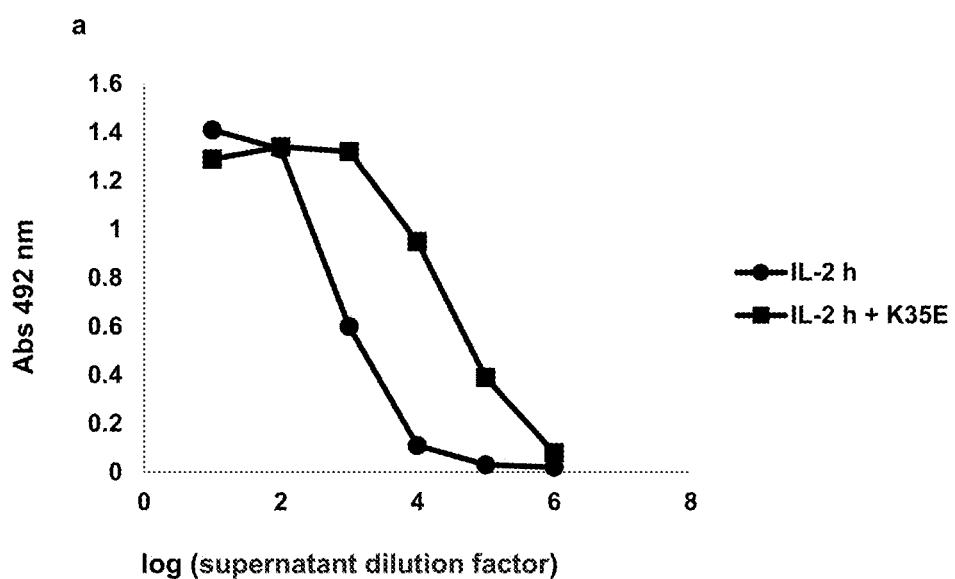
FIG. 2. ELISA evaluation of the secretion levels of fusion proteins formed by either IL-2 or its derived muteins and human IgG1 Fc domain. Cells were transfected with polyethylenimine and the genetic constructs coding for fusion proteins that contain:
    a. IL-2 with and without the mutation K35E
    b. No-alpha IL-2 (NA) with and without the additional mutation K35E
    c. Super-beta IL-2 (SB) with and without K35E
    d. No-gamma M1 IL-2 (NG M1) with and without K35E
    e. No-gamma M2 IL-2 (NG M2) with and without K35E FIG. 3. Conservation of the molecular interactions of native IL-2 in the K35E variant (ELISA).
Figure 2:
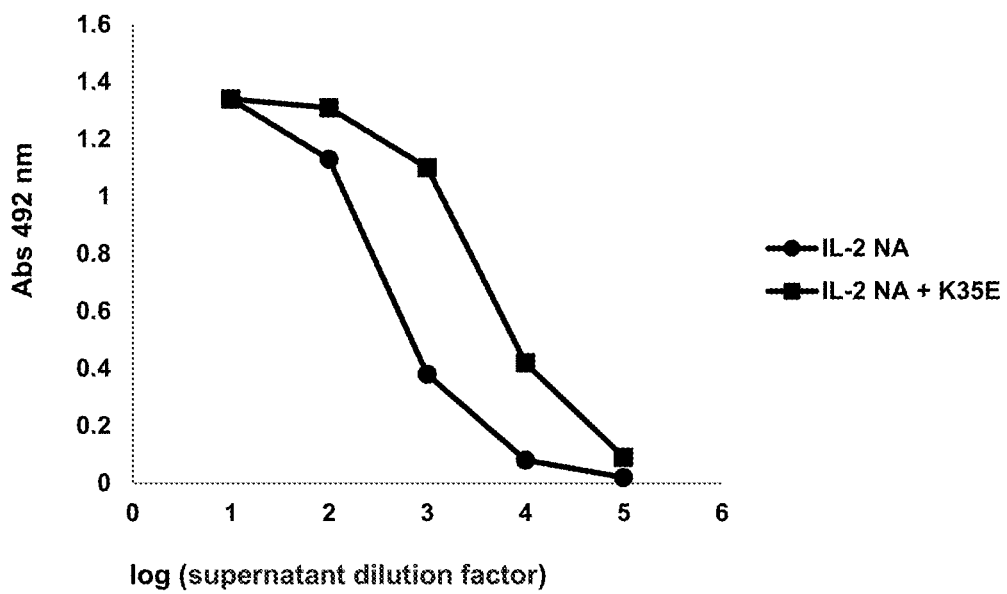
Figure 2:
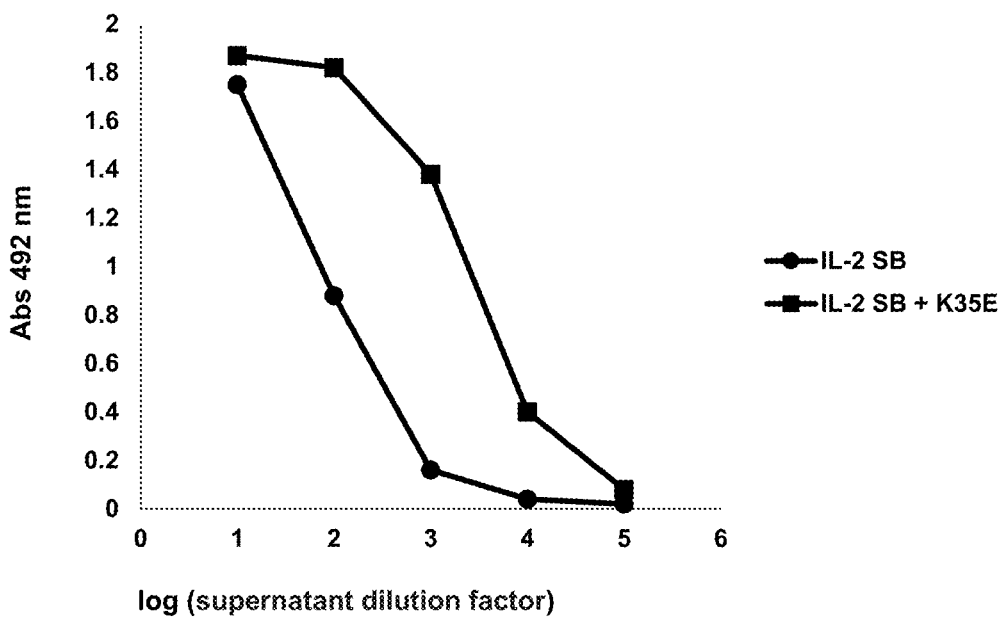
Figure 2:
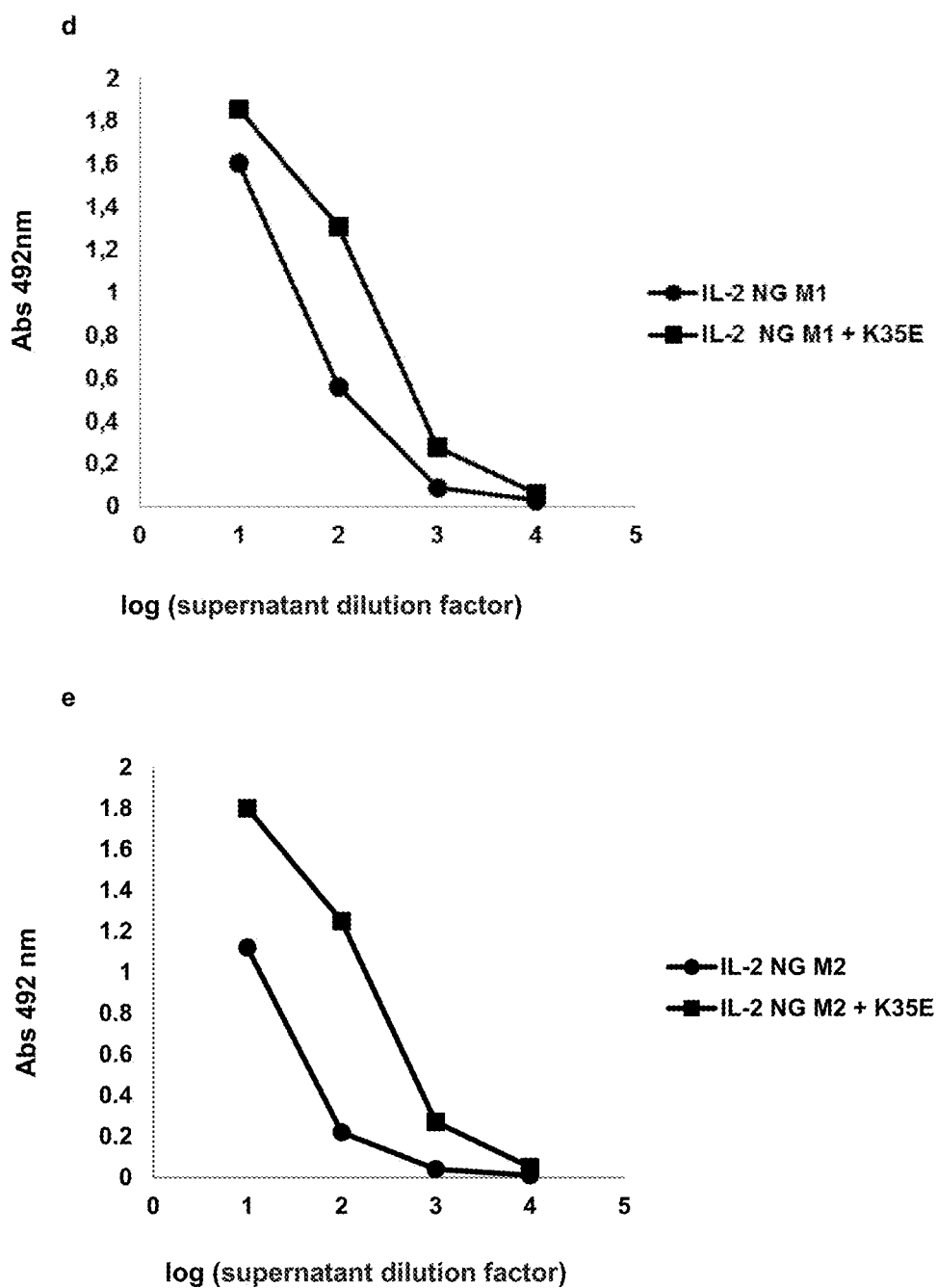

The ability of different IL-2 variants selected from the library to be secreted to *E. coli* periplasm and displayed on phages was compared. Native IL-2 was used as reference molecule. The K35R-containing variant (conservative change at position 35) was also constructed by Kunkel mutagenesis to be used as an additional control. All the proteins were obtained through the insertion of their coding genes in the phagemid vector pCSM (fused to M13 gene 3) and subsequent phage production from TG1 bacteria transformed with the resulting genetic constructs (Rojas, G. et al, Immunobiology. 218: 105-113, 2013). The levels of phage display of each variant were evaluated through an ELISA on microtitration plates coated with 9E10 monocional antibody. Bound phages were detected with an anti-M13 antibody coupled to horseradish peroxidase. It was shown that replacements K35E, K35D and K35Q result in an increase of the display of human IL-2 as compared with the original molecule (FIG. 1). The magnitude of this increase was 10-fold for charge inversion changes K35E and K35D, and 7-fold for K35Q. On the other hand, the conservative change K35R did not modify the ability of IL-2 to be displayed (FIG. 1). K35E was chosen for further studies.

Example 3. The Effect of K35E Replacement on Secretion and Phage Display Extends to a Panel of IL-2 Mutated Variants K35E was introduced by Kunkel mutagenesis in the genes of several mutated variants of human IL-2 (in the phage-displayed format). The panel included four muteins already described to perform different immunomodulatory functions: one no-alpha mutein with selective agonist function on effector T cells (Carmenate, T. et al, J. Immunol. 190: 6230-6238, 2013; U.S. Pat. No. 9,206,243 B2), one antagonist mutein that loses its binding ability to the gamma IL-2 receptor subunit (no-gamma) (U.S. Pat. No. 8,759,486 B2), and two superagonist muteins with enhanced binding ability to either beta (super-beta) or alpha (super-alpha) IL-2 receptor subunits (Levin, A. M. et al, Nature. 484: 529-533, 2012; WO 2005/007121). Phages displaying each of these proteins were produced and purified (together with the original molecules without K35E), and the display levels of the foreign proteins were evaluated by ELISA on microtitration plates coated on with the 9E10 monoclonal antibody. A phage preparation displaying native IL-2 was used as reference (assuming the presence of 100 arbitrary units/ml in it) to construct a standard curve in order to calculate the relative display levels for each variant. Table 1 shows the increase in the display level of each mutein associated to the introduction of K35E.

TABLE 1

Increase in the display levels of tested muteins associated to the introduction of the replacement K35E.

| Mutein | Increase in the relative phage display levels associated with the introduction of K35E |
|---|---|
| No-alpha | 6x |
| No-gamma M1 | 29x |
| Super-beta H9 | 18x |
| Super-alpha | 14x |

Example 4. The Replacement K35 Enhances the Secretion of Fusion Proteins Based on IL-2 and its Derived Muteins by Human Host Cells Genetic constructs were designed to fuse the genes of human IL-2 and its derived muteins to the human IgG1 Fc region gene, in the context of the pCMX expression vector. An additional panel of equivalent constructs having the mutation K35E was also prepared. HEK 293 T cells (adapted to grow in suspension) were transfected with each of the above described genetic constructs properly mixed with polyethyleneimine. The transfection volume was 50 ml. Supernatants from transfected cells were collected after six days of culture. The presence of the recombinant IL-2-derived proteins was evaluated by ELISA on microtitration plates coated with IL-2.2 monoclonal antibody (directed against a linear epitope present on all the muteins). Captured fusion proteins were detected with an anti-human Fc antibody coupled to horseradish peroxidase. The levels of fusion proteins in the supernatants were higher for those molecules containing the replacement K35E as compared with their original counterparts (FIG. 2*a-e*). Such recombinant proteins were purified by Protein A affinity chromatography. Table 2 shows the yields after purification.

TABLE 2

Purification yields of IL-2 and its derived muteins fused to Fc domain of human immunoglobulins from HEK 293 T cells transfected in suspension.

| Molecule | Original variant | K35E variant | K35E-associated increase |
| --- | --- | --- | --- |
| IL-2/Fc | 0.28 mg | 4.24 mg | 15x |
| No-alpha/Fc | 0.16 mg | 1.44 mg | 9x |
| Super-alpha/Fc | 1.72 mg | 5.08 mg | 3x |
| Super-beta/Fc | 0.04 mg | 1.08 mg | 27x |
| No-gamma M1/Fc | 0.04 mg | 0.24 mg | 6x |
| No-gamma M2/Fc | 0.04 mg | 0.2 mg | 5x |

Example 5. K35E Replacement is Compatible with the Molecular Interactions of Native IL-2

Figure 3:
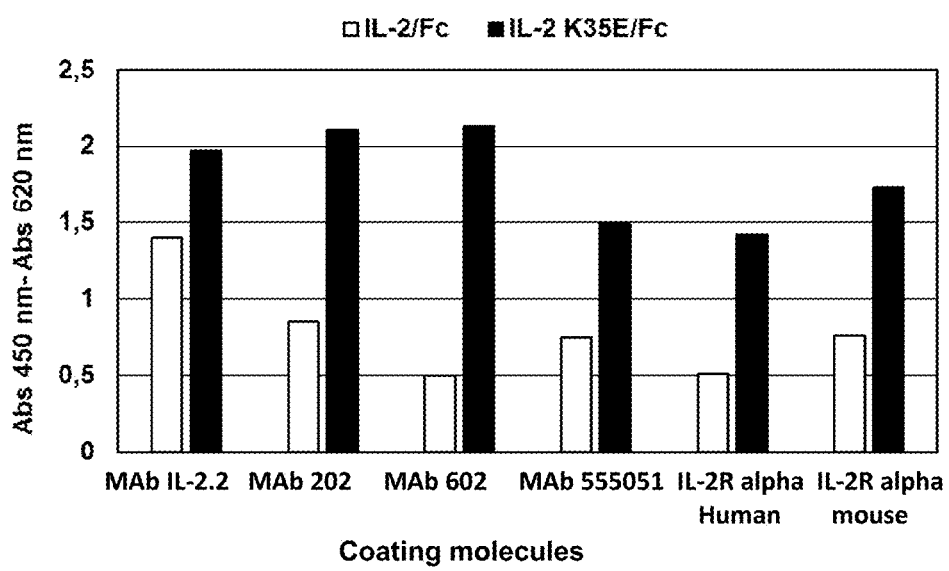

The binding ability of recombinant mutated IL-2 (K35E) in the human Fc-fused homodimer format was evaluated by ELISA on microtitration plates coated with different molecules known to interact with native IL-2. The panel of coating molecules included four monoclonal antibodies that recognize different epitopes on IL-2, as well as the IL-2 receptor alpha subunit (of human or mouse origin). The captured fusion protein was detected with an anti-human Fc antibody coupled to horseradish peroxidase. A similar fusion homodimer including non-mutated IL-2, produced in the same expression system, was used as the control. Binding of the mutated homodimer to both the antibodies and the receptors was not affected by the presence of K35E, on the contrary it produced the opposite effect. Reactivity of the mutated variant towards all the coating molecules was higher than that of its non-mutated recombinant counterpart (FIG. 3), which indicates that the antigenicity and functionality of the K35E variant reproduce those of the native IL-2 to a greater extent than those of the non-mutated recombinant protein obtained under similar conditions.

Figure 4:
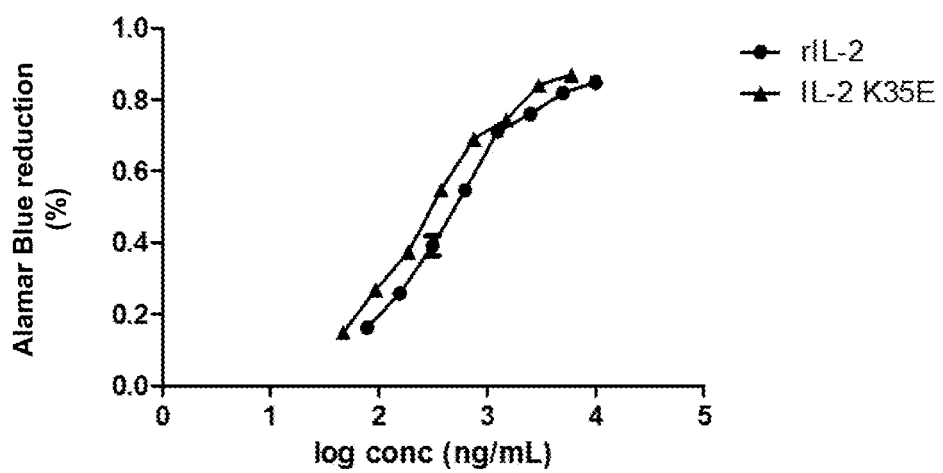
FIG. 4. Conservation of IL-2 biological activity with the replacement K35E using a CTLL-2 proliferation assay.

Example 6. Fc-Fused IL-2 K35E Maintains the Ability to Stimulate the Proliferation of CTLL-2 Cells The ability of mutated IL-2 (K35E) in the Fc-fused homodimer format (purified from HEK 293 T cells transfected in suspension) to induce CTLL-2 proliferation was evaluated. Recombinant human IL-2 was used as the control. Cells were grown in the presence of different concentrations of both proteins, and proliferation was measured through the colorimetric Alamar blue reduction assay (FIG. 4). The specific activity was calculated in every case from the dose of the molecule that produced half-maximal proliferation using GraphPad software. Specific activity of Fc-fused mutated IL-2 (including K35E) was $4 \times 10^6$ IU/mg, in the same range than that of the reference recombinant IL-2 ($2,3 \times 10^6$ IU/mg). This result showed the conservation of IL-2 biological activity in the presence of K35E.

Figure 5:
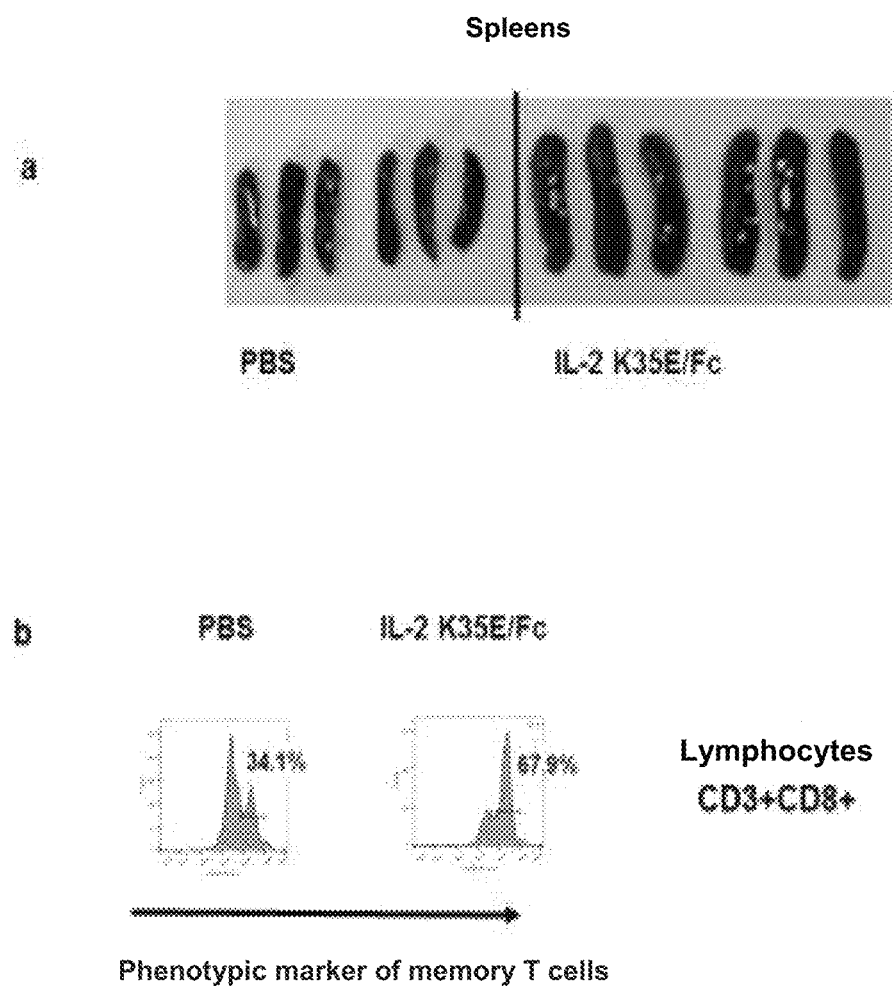
FIG. 5. Ability of IL-2 K35E to expand IL-2-dependent cell populations in vivo.
    5a. Photograph of the spleens of mice injected with IL-2 K35E variant and PBS.
    5b. Flow cytometry histograms of CD3+CD8+ memory phenotype (CD44hi) cell population in the spleens.

Example 7. Fc-Fused IL-2 K35E has the Ability to Stimulate the Expansion of Memory Phenotype CD8 T Cells In Vivo C57BL/6 mice received five daily doses of $4 \times 10^4$ IU of Fc-fused mutated IL-2 (K35E) during 5 consecutive days to study the ability of this protein to stimulate in vive proliferation of IL-2-dependent cell populations. The animals were sacrificed after the treatment and their spleens were observed. Additionally, the size of the population of CD3+ CD8+ cells having memory phenotype (CD44hi) was determined by flow cytometry. The control of the experiment was a group of mice injected with phosphate buffered saline (PBS). The recombinant Fc-fused IL-2 (K35E) had the expected effect on memory CD8 T cell population, as judged by the enlargement of spleens (FIG. 5a) and the duplication of the proportion of memory phenotype CD8 T cells within them (FIG. 5b).

Figure 6:
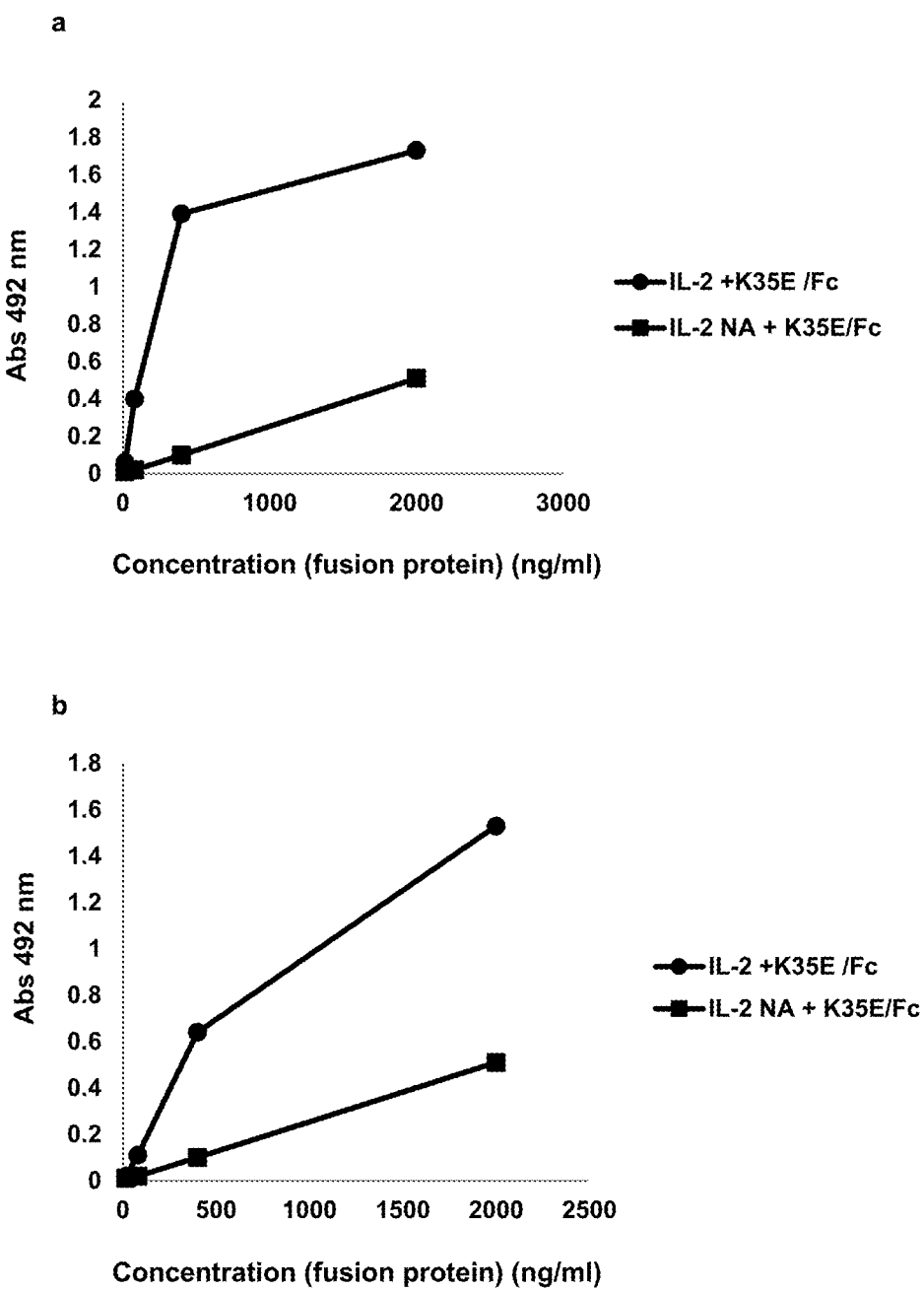
FIG. 6. Compatibility of the replacement K35E with the loss of binding ability to the IL-2 receptor alpha subunit already described for an IL-2-derived mutein (ELISA). Microtitration plates were coated with human (a) and mouse (b) alpha subunit.

Example 8. The Replacement K35E is Compatible with the Loss of Binding Ability to the IL-2 Receptor Alpha Subunit that Determines the Properties of a Selective Agonist The binding properties of both human IL-2 and of a no-alpha mutein previously described (Carmenate, T. et al, J. Immunol. 190: 6230-6238, 2013; U.S. Pat. No. 9,206, 243), which contains the replacements R38A, F42A, Y45A and E62A resulting in a loss of ability to bind the IL-2 receptor alpha subunit aimed at reducing its stimulatory potential on T regulatory cells without affecting the action on effector cells having the heterodimeric beta/gamma receptor, were compared. Both recombinant proteins had the additional K35E mutation and were produced as fusion proteins containing the Fc domain of human immunogiobulins. Microtitration plates were coated with the recombinant IL-2 receptor alpha subunit of human (a) and mouse (b) origin. Captured fusion proteins were detected with an anti-human Fc antibody coupled to horseradish peroxidase. The introduction of K35E gave rise to a new no-alpha molecule with expression levels higher than those of its original counterpart (FIG. 2b) and a severe reduction in human and mouse alpha chain binding as compared to the non-mutated IL-2 also having the replacement K35E (FIG. 6). These results rendered the first evidences of the compatibility of K35E with the selective modulation of the interactions and immunomodulatory functions of IL-2.

Example 9. The Replacement K35E is Compatible with the Increase in IL-2 Receptor Beta Subunit Binding Ability Already Described for a Superagonist Variant The binding ability of IL-2 and a super-beta mutein containing the mutations L80F, R81 D, L85V, I86V and I92F (both with the additional mutation K35E and fused to the Fc domain of human IgG1) was evaluated by ELISA on plates coated with the IL-2 receptor beta subunit. Captured fusion proteins were detected with an anti-human Fc antibody coupled to horseradish peroxidase. The introduction of K35E gave rise to a new molecule with higher expression levels as compared to the original super-beta mutein (FIG. 2c) and with enhanced beta subunit binding ability, which is the basis for its superagonist function (FIG. 7). This result expanded the evidences of compatibility of the K35E replacement with the design of new IL-2-derived molecules with modifications in their interactions with receptor subunits and immunomodulatory functions.

The invention claimed is:

1. A method for introducing a mutation that causes increased secretion of recombinant human IL-2 from a host cell, the method comprising introducing i) a non-conservative mutation at position 35 of the primary sequence of the recombinant human IL-2 and ii) one or more additional mutations, thereby producing a polypeptide comprising a recombinant human IL-2 derived mutein,
   wherein the non-conservative mutation at position 35 is selected from the group consisting of:
   K35E, K35D and K35Q,
   and
   wherein the recombinant human IL-2 derived mutein has an amino acid sequence selected from the group consisting of:
   SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18.

2. The method according to claim 1, wherein the polypeptide comprises the recombinant human IL-2 derived mutein fused to a protein selected from the group consisting of:
   a capsid protein of the filamentous phages,
   albumin,
   an Fc region of an antibody,
   a whole antibody, and
   an antibody fragment including its variable domains.

3. The method according to claim 1, wherein the host cell is selected from the group consisting of:
   an *E. coli* cell,
   a mammalian cell, and
   a yeast cell.

4. A polypeptide comprising a recombinant human IL-2 derived mutein selected from the group consisting of:
   SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18.

5. A method for increasing secretion of recombinant human IL-2 from a host cell, the method comprising expressing in the host cell a polypeptide comprising a recombinant human IL-2 derived mutein,
   wherein the recombinant human IL-2 derived mutein comprises i) a non-conservative mutation at position 35 of the primary sequence of the recombinant human IL-2 and ii) one or more additional mutations,
   wherein the non-conservative mutation at position 35 is selected from the group consisting of:
   K35E, K35D and K35Q,
   and
   wherein the recombinant human IL-2 derived mutein has an amino acid sequence selected from the group consisting of:
   SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18.

6. The method according to claim 5, wherein the recombinant human IL-2 derived mutein is fused to a protein selected from the group consisting of:
   a capsid protein of a filamentous phages,
   albumin, an Fc region of an antibody,
a whole antibody, and
an antibody fragment including its variable domains.

7. The method according to claim 5, wherein the host cell is selected from the group consisting of:
an *E. coli* cell,
a mammalian cell, and
a yeast cell.

8. The method according to claim 5, wherein the host cell is selected from the group consisting of:
an NK cell,
a T lymphocyte, and
a B lymphocyte.

9. A method for introducing a mutation that causes increased secretion of recombinant human IL-2 from a host cell, the method comprising introducing i) a non-conservative mutation at position 35 of the primary sequence of the recombinant human IL-2 and ii) one or more additional mutations, thereby producing a polypeptide comprising a recombinant human IL-2 derived mutein,
wherein the non-conservative mutation at position 35 is K35E
and
wherein the recombinant human IL-2 derived mutein has the amino acid sequence of SEQ ID NO: 7.

10. The method according to claim 9, wherein the recombinant human IL-2 derived mutein is fused to a protein selected from the group consisting of:
a capsid protein of a filamentous phages,
albumin,
an Fc region of an antibody,
a whole antibody, and
an antibody fragment including its variable domains.

11. The method according to claim 9, wherein the host cell is selected from the group consisting of:
an *E. coli* cell,
a mammalian cell, and
a yeast cell.

12. The method according to claim 9, wherein the host cell is selected from the group consisting of:
an NK cell,
a T lymphocyte, and
a B lymphocyte.

13. A method for increasing secretion of recombinant human IL-2 from a host cell, the method comprising expressing in the host cell a polypeptide comprising a recombinant human IL-2 derived mutein,
wherein the recombinant human IL-2 derived mutein comprises i) a non-conservative mutation at position 35 of the primary sequence of the recombinant human IL-2 and ii) one or more additional mutations,
wherein the non-conservative mutation at position 35 is K35E
and
wherein the recombinant human IL-2 derived mutein has the amino acid sequence of SEQ ID NO: 7.

14. The method according to claim 13, wherein the recombinant human IL-2 derived mutein is fused to a protein selected from the group consisting of:
a capsid protein of a filamentous phages,
albumin,
an Fc region of an antibody,
a whole antibody, and
an antibody fragment including its variable domains.

15. The method according to claim 13, wherein the host cell is selected from the group consisting of:
an *E. coli* cell,
a mammalian cell, and
a yeast cell.

16. The method according to claim 13, wherein the host cell is selected from the group consisting of:
an NK cell,
a T lymphocyte, and
a B lymphocyte.

17. The method according to claim 1, wherein the host cell is selected from the group consisting of:
an NK cell,
a T lymphocyte, and
a B lymphocyte.

18. The polypeptide according to claim 4, wherein the polypeptide comprises the recombinant human IL-2 derived mutein fused to a protein selected from the group consisting of:
a capsid protein of a filamentous phages,
albumin,
an Fc region of an antibody,
a whole antibody, and
an antibody fragment including its variable domains.

* * * * *

UNITED STATES PATENT AND TRADEMARK OFFICE
CERTIFICATE OF CORRECTION

| | |
|---|---|
| PATENT NO. | : 12,312,388 B2 |
| APPLICATION NO. | : 16/461258 |
| DATED | : May 27, 2025 |
| INVENTOR(S) | : Gertrudis Rojas Dorantes et al. |

Page 1 of 1

It is certified that error appears in the above-identified patent and that said Letters Patent is hereby corrected as shown below:

In the Claims

In Claim 2, at Column 27, Line 58, replace "the filamentous phages" with --a filamentous phage--.

In Claim 6, at Column 28, Line 66, replace "a filamentous phages" with --a filamentous phage--.

In Claim 10, at Column 29, Line 29, replace "a filamentous phages" with --a filamentous phage--.

In Claim 14, at Column 30, Line 16, replace "a filamentous phages" with --a filamentous phage--.

In Claim 18, at Column 30, Line 40, replace "a filamentous phages" with --a filamentous phage--.

Signed and Sealed this
Thirtieth Day of December, 2025

John A. Squires
*Director of the United States Patent and Trademark Office*